(12) United States Patent
Tomita et al.

(10) Patent No.: US 7,083,608 B2
(45) Date of Patent: Aug. 1, 2006

(54) MEDICAL APPARATUS AND MEDICAL SYSTEM

(75) Inventors: Seiki Tomita, Gamagori (JP); Koshu Tajitsu, Nukata-gun (JP); Hidenori Kanda, Okazaki (JP)

(73) Assignee: Nidek Co., Ltd. (JP)

( * ) Notice: Subject to any disclaimer, the term of this patent is extended or adjusted under 35 U.S.C. 154(b) by 554 days.

(21) Appl. No.: 09/893,969

(22) Filed: Jun. 29, 2001

(65) Prior Publication Data
US 2002/0002368 A1    Jan. 3, 2002

(30) Foreign Application Priority Data
Jun. 30, 2000   (JP)   .............................. 2000-203037

(51) Int. Cl.
*A61B 18/04*    (2006.01)
(52) U.S. Cl. ............................... 606/4; 606/34; 606/41
(58) Field of Classification Search ................ 606/4–6, 606/1, 41
See application file for complete search history.

(56) References Cited
U.S. PATENT DOCUMENTS

| | | | |
|---|---|---|---|
| 4,837,857 A * | 6/1989 | Scheller et al. ............. | 398/113 |
| 5,147,349 A * | 9/1992 | Johnson et al. ................ | 606/4 |
| 5,157,603 A * | 10/1992 | Scheller et al. ................ | 606/4 |
| 5,423,798 A * | 6/1995 | Crow ............................ | 606/4 |
| 5,455,766 A * | 10/1995 | Scheller et al. ................ | 606/4 |
| 6,010,496 A * | 1/2000 | Appelbaum et al. ........... | 606/4 |
| 6,027,493 A * | 2/2000 | Donitzky et al. .............. | 606/4 |
| 6,117,126 A * | 9/2000 | Appelbaum et al. ........... | 606/1 |

FOREIGN PATENT DOCUMENTS

JP         10-283152         10/1998

OTHER PUBLICATIONS

Brochure of Nidek Co., Ltd., CV-24000, specifications and design.
Brochure of Nidek Co., Ltd., GYC-2000, specifications and design.

* cited by examiner

*Primary Examiner*—Roy D Gibson
*Assistant Examiner*—Henry M. Johnson, III
(74) *Attorney, Agent, or Firm*—Rader, Fishman & Grauer, PLLC

(57) ABSTRACT

A medical system capable of giving different treatments in a row to a patient comprises a first treatment apparatus, a second treatment apparatus, an operation unit, a memory, a communication unit and a selection switch. The first treatment apparatus has a first treatment unit for a first treatment and a first control part which sends a control signal to the first treatment unit based on a first setting signal for the first treatment. The second treatment apparatus has a second treatment unit for a second treatment different from the first treatment and a second control part which sends a control signal to the second treatment unit based on a second setting signal for the second treatment. The operation unit has an indication part and an operation part, and is capable of inputting the first and second setting signals at different times, and the two signals are then transmitted to the first and second control parts respectively by the communication unit. The memory is capable of storing two groups of data, one of which concerns a first operating screen for the first treatment and the other concerns a second operating screen for the second treatment. Any one of the two groups of data is selectively read from the memory and displayed on the indication part, based on a mode-selection signal which has been inputted through the selection switch for selecting any one of a first-treatment mode and a second-treatment mode.

3 Claims, 4 Drawing Sheets

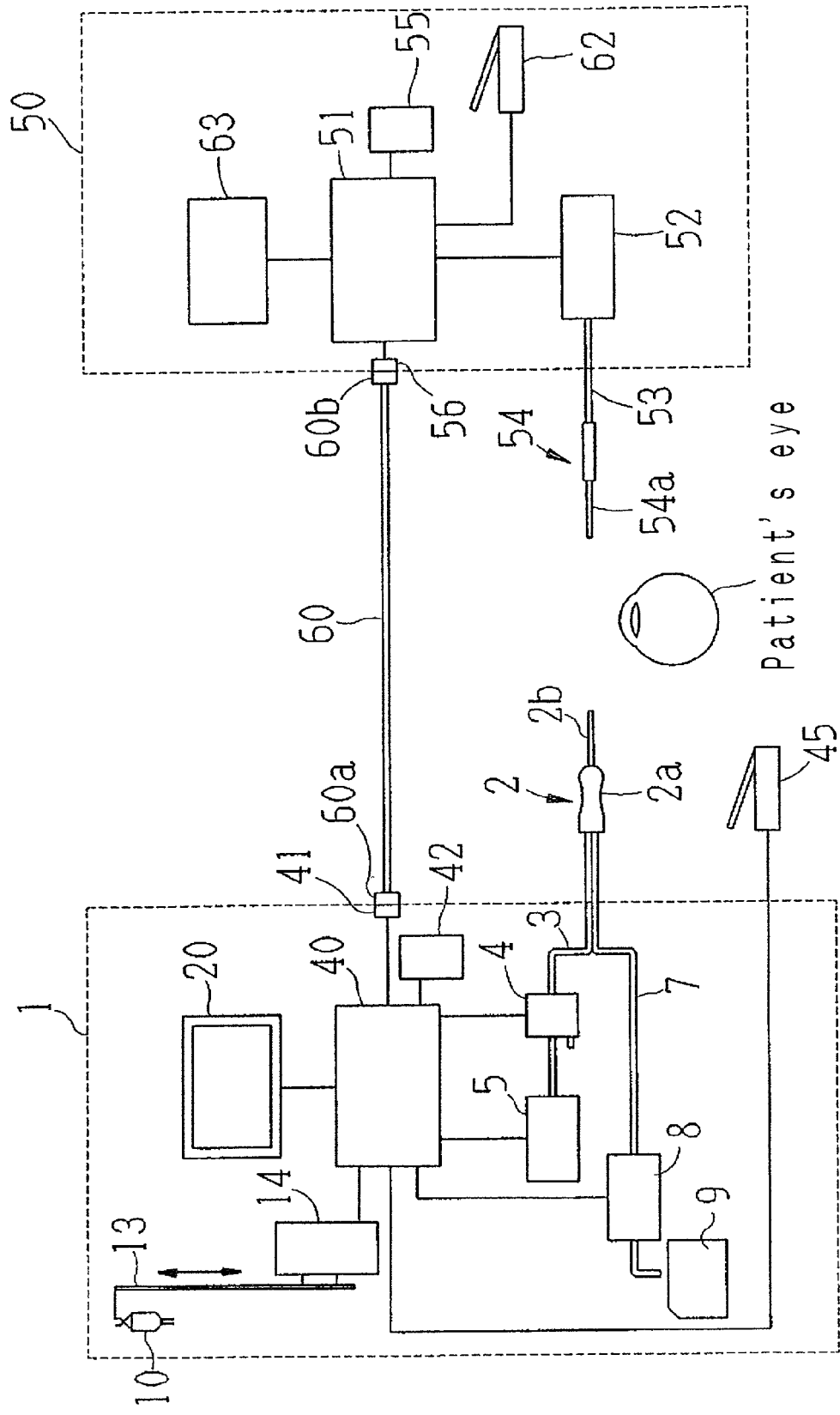
F I G. 2

MEDICAL APPARATUS AND MEDICAL SYSTEM

BACKGROUND OF THE INVENTION

1. Field of the Invention

The present invention relates to a medical apparatus and a medical system suitable for giving different treatments in a row to a patient.

2. Description of Related Art

In some of the cases where a remedy (surgery) is conducted on a patient, two or more apparatuses are consecutively used to give him different treatments in a row. In the field of ophthalmology, for example, in a remedy against retinal detachment, a vitreous body of a patient is cut and aspirated through the use of a vitrectomy apparatus having a cutter for cutting vitreous bodies. Subsequently, a laser beam from a laser photocoagulating apparatus is guided into an eye of the patient, and then is irradiated on the part suffering from retinal detachment so that a coagulation treatment is conducted. Thus, the photocoagulating apparatus is prepared in an operating room as well as the vitrectomy apparatus. Each apparatus comprises an operation panel having a variety of keys (buttons) for setting surgical conditions and the like, a foot switch for outputting signals to operate the apparatus, and the like.

However, in the case of consecutive use of those apparatuses, it is annoying and difficult to handle two operation panels independently mounted on the respective apparatuses positioned separately from each other. In addition, if the foot switches of the two apparatuses are placed next to each other at a surgeon's feet, he is liable to mix up the two foot switches. Besides, in some cases, another foot switch, which is for a surgical microscope, may be placed at his feet as well. It is also annoying and confusing to have this additional foot switch together with the two above-stated foot switches at the same time, because as many as three foot switches make a nuisance taking up too much room. On the other hand, it is too troublesome to replace a foot switch of one apparatus with that of another when needed.

SUMMARY OF THE INVENTION

The present invention has been made in view of the above circumstances and has an object to overcome the above problems and to provide a medical apparatus and a medical system capable of improving operability of the apparatus and saving more space in an operating room.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, a medical system for giving different treatments in a row to a patient comprises a first treatment apparatus, a second treatment apparatus, an operation unit, a memory, a communication unit and a selection switch. The first treatment apparatus has a first treatment unit for a first treatment and a first control part which sends a control signal to the first treatment unit based on a first setting signal for the first treatment. The second treatment apparatus has a second treatment unit for a second treatment different from the first treatment and a second control part which sends a control signal to the second treatment unit based on a second setting signal for the second treatment. The operation unit has an indication part and an operation part, and is capable of inputting the first setting signal and the second setting signal at different times. The memory is capable of storing data concerning a first operating screen for the first treatment and data concerning a second operating screen for the second treatment. The communication unit transmits the first setting signal and the second setting signal from the operation unit to the first control part and the second control part respectively. The selection switch is used to input a mode-selection signal to select any one of a first-treatment mode and a second-treatment mode. Based on the inputted mode-selection signal, any one of the first-operating-screen data and the second-operating-screen data is selectively read from the memory and displayed on the indication part.

In another aspect of the present invention, as embodied and broadly described herein, a medical apparatus, which has a first treatment unit for a first treatment and is connectible with a second medical apparatus having a second treatment unit for a second treatment different from the first treatment, comprises an operation unit, a first memory, a selection switch and a control part. The operation unit has an indication part and an operation part, and is capable of inputting a first setting signal and a second setting signal at different times. The first memory stores data concerning a first operating screen for the first treatment. The selection switch is used to input a mode-selection signal to select any one of a first-treatment mode and a second-treatment mode. Based on the first setting signal, the control part sends a control signal to the first treatment unit. Based on the inputted mode-selection signal, the control part reads any one of the two groups of data; that is, the data concerning the first operating screen to be read from the first memory, and data concerning the second operating screen for the second treatment to be read from a second memory of the second medical apparatus, so that the read data is displayed on the indication part.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 2 is a view showing a schematic configuration of a control system in the medical system;

DETAILED DESCRIPTION OF THE PREFERRED EMBODIMENTS

Figure 1:
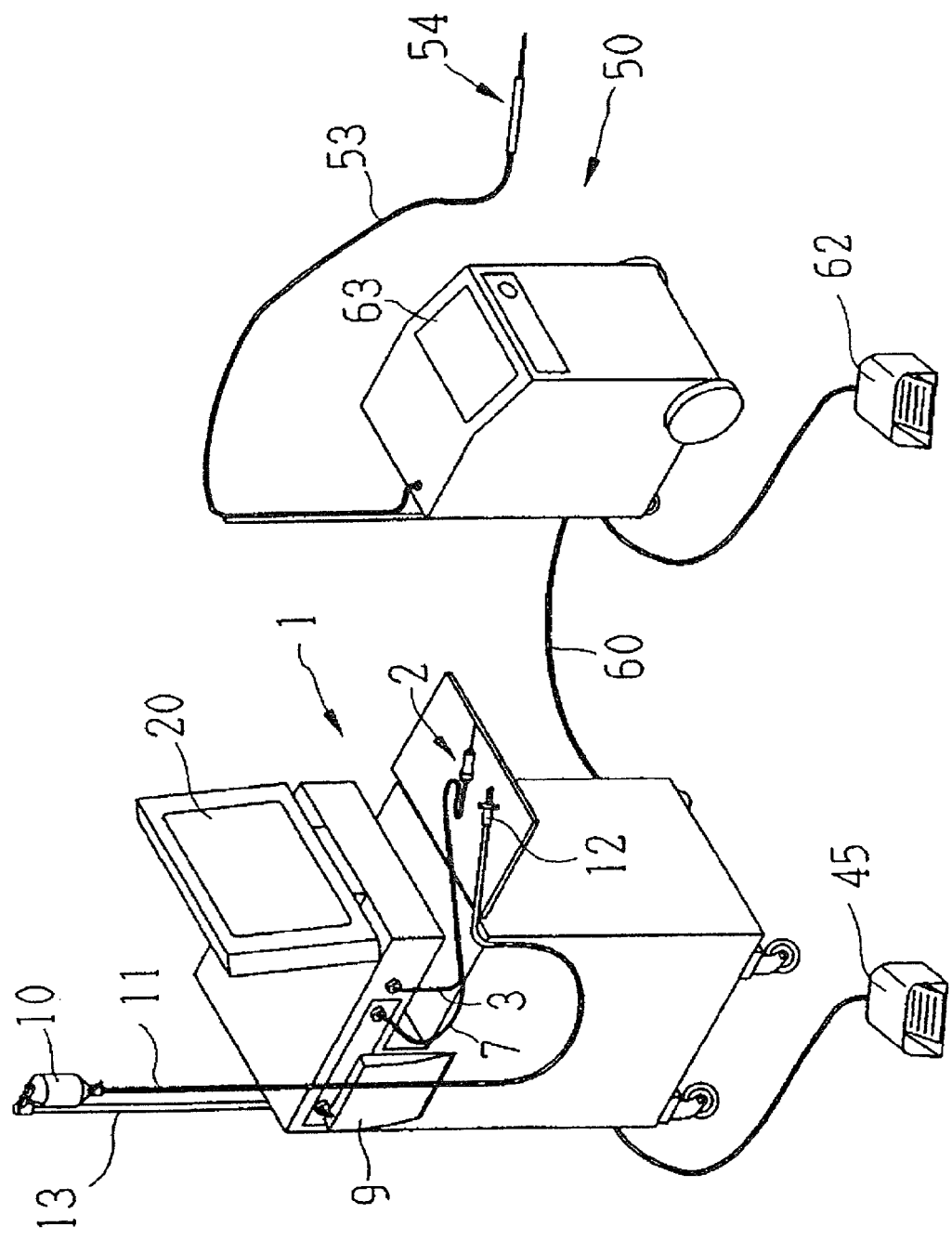
FIG. 1 is a view showing a schematic configuration of a medical system as one preferred embodiment according to the present invention in which a vitrectomy apparatus and a laser photocoagulating apparatus are used in combination.

A detailed description of one preferred embodiment of the present invention will now be given referring to the accompanying drawings. FIG. 1 is a view showing a schematic configuration of a medical system being the present embodiment in which a vitrectomy apparatus 1 and a laser photocoagulating apparatus 50 are used in combination. FIG. 2 is a view showing a schematic configuration of a control system in the medical system.

The vitrectomy apparatus 1 comprises a cutter 2 which a surgeon holds to cut a vitreous body. The cutter 2 aspirates a vitreous body from an aspiration hole of an outer cylinder 2b fixed on a housing 2a, and fits the aspirated part of the vitreous body into the cylinder 2b such that the vitreous body may be cut by reciprocating an inner blade within the outer cylinder 2b. The inner blade of the cutter 2 is pneumatic, reciprocated by alternate supply and discharge of compressed air. Connected to the cutter 2 is an air tube 3, which is also connected to an air pump 5 (compressor) via a magnetic valve 4. The compressed air is supplied to, and discharged from the cutter 2 through the tube 3 that is brought into contact with the pump 5 and the atmosphere alternately by actuation of the valve 4.

In addition, an aspiration tube 7 is connected to the cutter 2. By actuation of an aspiration pump 8, the cut portion of the vitreous body is aspirated along with an irrigation fluid which has been supplied to the inside of a patient's eye (an eye to be operated) so as to be flushed away into a waste fluid bag 9. The irrigation fluid within an irrigation bottle 10 is supplied into the eye through an irrigation tube 11 and a cannula 12. The bottle 10 is hung down from a pole 13, which is moved vertically by a vertical-motion drive unit 14 constituted of motors and the like. Pressure of the irrigation fluid is adjusted by changing a vertical position of the bottle 10.

Figure 3A:
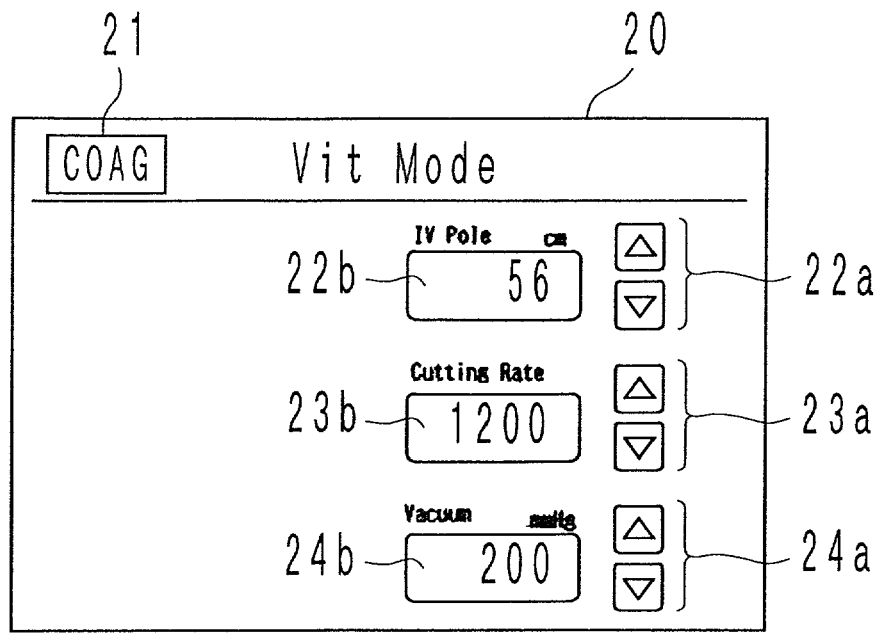
FIGS. 3A and 3B are views showing the respective examples of a screen displayed on an operation panel in vitrectomy mode and that in photocoagulation mode.

Provided at the front of the apparatus 1 is an operation panel 20. The panel 20 is a color liquid crystal touch panel, which displays an operating screen including a variety of keys (buttons) for changing surgical conditions, such as a cutting rate of the cutter 2 (a moving speed of the inner blade), an aspiration flow rate of the pump 5, and the vertical position of the bottle 10 (a height of the pole 13), and an indication part for displaying the conditions (see FIG. 3A.) On the panel 20, the operating screen for use with the apparatus 1 may change over to an operating screen for use with the apparatus 50 (see FIG. 3B) when a mode-selection key (button) 21 is touched. (This will be described later in detail.)

Reference numeral 45 is a foot switch for inputting signals to a control part 40 so as to activate an aspiration system including the cutter 2, the pump 5 and the like. The foot switch 45 is shared as a foot switch of the apparatus 50.

The valve 4, the pumps 5 and 8, and the drive unit 14 are connected with the control part 40 of the apparatus 1 and they are actuated under control of the control part 40. The control part 40 is also connected with the panel 20 and exercises control over screen displays on the panel 20 and signals from a touch sensor corresponding with the displays on the touch panel.

Housed in the main body of the laser photocoagulating apparatus 50 is a laser beam source part 52 for emitting a laser beam for photocoagulation formed by converting a fundamental wave with a wavelength of 1064 nm beamed out from Nd:YAG into a wavelength of 532 nm. The laser beam is guided to the tip 54a of an end-photo probe 54 held by the surgeon. The beam source part 52 is connected with a control part 51 of the apparatus 50, and is actuated under control of the control part 51.

The control parts 40 and 51 are mutually connected via a signal cable 60, allowing two-way communications. The connections with the cable 60 are established in such a manner that a connector 60a of the cable 60 is attached to a connector 41 connected with the control part 40 and that a connector 60b of the cable 60 is attached to a connector 56 connected with the control part 51. Incidentally, this connection may be wireless through optical communications.

Connected to the control part 40 is a memory 42 in which data concerning an operating screen in vitrectomy mode is stored. Connected to the control part 51 is a memory 55 in which data concerning an operating screen in photocoagulation mode is stored.

The apparatus 50, in turn, comprises an exclusive foot switch 62 and an operation panel 63 having a variety of keys (buttons) for setting laser irradiative conditions and an indication part for displaying the set conditions. The foot switch 62 and the operation panel 63 are configured such that they may be connected with, and disconnected from the control part 51 as desired.

Next, description will be given to operation of the present system.

The cable 60 is used to connect the apparatuses 1 and 50 both being placed in an operating room, and the foot switch 45 is placed at a surgeon's feet for operational ease. The apparatus 50 is activated with its unillustrated key switch while the apparatus 1 is activated with its unillustrated power switch, so that both apparatuses are put on standby. Then, the control part 40 calls up the vitrectomy-mode operating screen from the memory 42 to the panel 20 (see FIG. 3A.)

In vitrectomy, the surgeon supplies an irrigation fluid to the inside of the patient's eye through the cannula 12, and performs vitrectomy using the cutter 2 while observing the eye with an unillustrated surgical microscope. He may set the surgical conditions such as the cutting rate at required levels using their corresponding keys (buttons) on the panel 20. More specifically, the vertical position of the bottle 10 (the irrigation pressure), the cutting rate of the cutter 2, and the aspiration flow rate of the pump 5 may be set at intended values with keys 22a, 23a and 24a respectively, and the set values then appear in their corresponding boxes 22b, 23b and 24b displayed on the indication part.

The foot switch 45, when operated by the surgeon, actuates the aspiration system including the inner blade of the cutter 2, the pump 5 and the like. Based on the signals inputted from the foot switch 45, the control part 40 exercises control over actuations of the valve 4, the pumps 5 and 8, and the drive unit 14 in accordance with the surgical conditions which have been set on the panel 20.

Subsequently, a photocoagulation treatment is conducted to proceed with the remedy for retinal detachment. Instead of the cutter 2, the surgeon inserts the tip 54a of the probe 54 into the inside of the eye, and takes other necessary steps. When the key 21 is touched on the panel 20, the control part 40 calls up the photocoagulation-mode operating screen from the memory 55 via the control part 51, so that the display on the panel 20 may change over to this operating screen (see FIG. 3B.) Thus, the surgeon (or his assistant) may immediately set the irradiative conditions required for the photocoagulation treatment. To be more concrete, laser output (laser power) and coagulating time (irradiating duration) may be set at intended values with keys 32a and 33a respectively, and the set values then appear in their corresponding boxes 32b and 33b displayed on the indication part. The vitrectomy-mode operating screen and the photocoagulation-mode operating screen may instantly be distinguished from each other if they are designed to have their respective backgrounds in mutually different colors.

Operation signals from the panel 20 in the photocoagulation mode are sent from the control part 40 to the control part 51 of the apparatus 50 via the cable 60.

In addition, the signals from the foot switch 45 are also inputted from the control part 40 to the control part 51 via the cable 60 when the system is switched over to the photocoagulation mode. Based on the signals inputted from the foot switch 45, the control part 51 actuates the beam source part 52 in accordance with the irradiative conditions which have been set on the panel 20. The laser beam from the beam source part 52 is guided to the probe 54, and then is irradiated from the tip 54a onto an affected part of the eye. Therefore, the surgeon is able to conduct both the vitrectomy and the photocoagulation treatment using the same foot switch 45. When he needs to revert from the photocoagulation to the vitrectomy, he may use the key 21 to do a changeover to the vitrectomy mode.

The control part 40 monitors via the cable 60 and the connectors whether signals may be communicated from the control part 51 or not. (The control part 40 senses signal communicability when it receives a confirmation signal from the control part 51.) In the case where communication of the confirmation signal from the control part 51 is broken off in the photocoagulation mode, the control part 40 alerts the surgeon to the communication break-off by displaying a warning message or making a warning beep. In the case where the communication of the confirmation signal from the control part 51 is broken off in the vitrectomy mode, the control part 40 also alerts him to disconnection and prevents misoperation by hiding the button 21 from the display screen so as to disable a changeover to the photocoagulation mode or by rejecting to call up the photocoagulation-mode operating screen.

Figure 4:
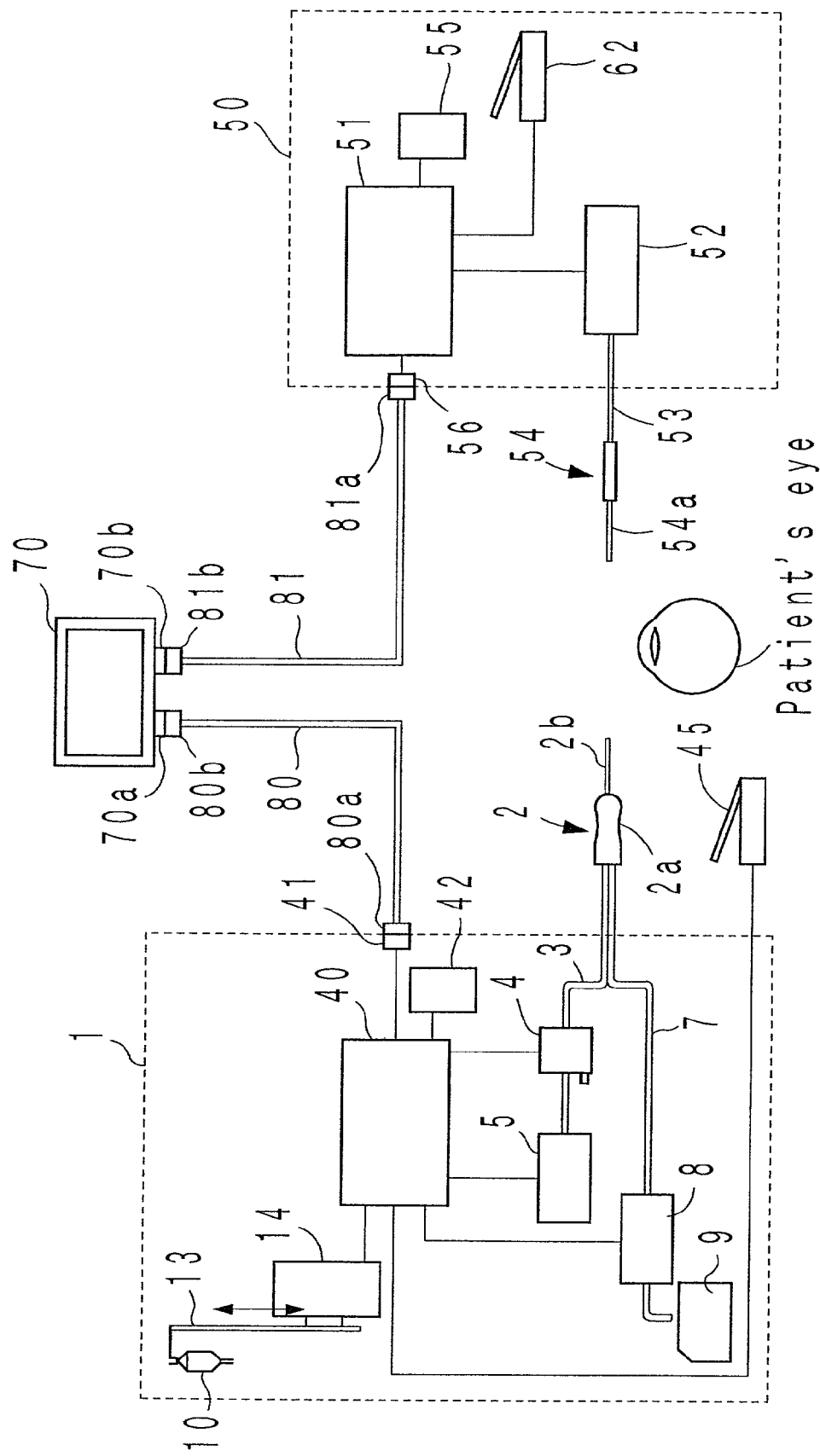
FIG. 4 is a view showing a schematic configuration of a control system in a modification of the medical system.

In addition, FIG. 4 shows one possible modification in which the control parts 40 and 51 are connected with an operation panel 70 through the use of cables 80 and 81 to ensure two-way communications. In this case, a connector 80a of the cable 80 is attached to the connector 41 connected to the control part 40, and a connector 80b of the cable 80 is attached to a connector 70a connected to the operation panel 70. Similarly, a connector 81a of the cable 81 is attached to the connector 56 connected to the control part 51, and a connector 81b of the cable 81 is attached to a connector 70b connected to the operation panel 70. Incidentally, this connections may also be wireless through optical communications. Thus, via the cable 80, the operation panel 70, the cable 81 and the connectors, the control parts 40 and 51 monitor whether signals may be communicated to each other or not. (Each of the control parts senses signal communicability when it receives a confirmation signal from the other.) In the case where the communication of the confirmation signal from the control part 51 is broken off in the vitrectomy mode, the control part 40 hides the button 21 from the display screen so as to disable the changeover to the photocoagulation mode. In the case where communication of the confirmation signal from the control part 40 is broken off in the photocoagulation mode, the control part 51 hides the button 21 from the display screen so as to disable the changeover to the vitrectomy mode.

In addition, the operation panel may contain a memory for storing both the data concerning the vitrectomy-mode operating screen and the data concerning the photocoagulation-mode operating screen, and may also incorporate an image-controlling unit for selecting between the two screens so as to bring up one of them onto the display screen.

Figure 3B:
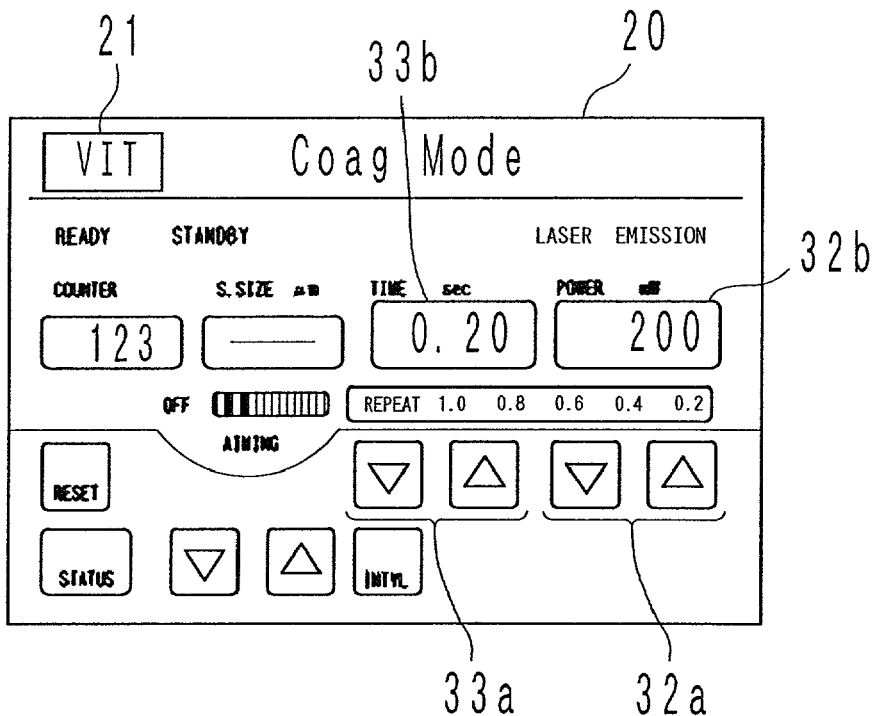

The above description has been given to an example of connecting the vitrectomy apparatus 1 and the laser photocoagulating apparatus 50 to use them as a system. The apparatus 50, however, may be used individually as well. In the case where the apparatus 50 is used for treating outpatients, for example, the apparatus 50 may be connected with a footswitch 62 and an operation panel 63 (which includes the same keys (buttons) and the same indication part as shown in FIG. 3B and yet which does not always have to be a liquid crystal touch panel), enabling input of the operation signals to the apparatus 50.

It should be noted that this invention is not be limited to the above-described system in which a vitrectomy apparatus and a laser photocoagulating apparatus are used in combination. Instead of combining two different treatment (surgery) apparatuses, for instance, it is possible to combine a measurement apparatus and a treatment (surgery) apparatus, such as a corneal shape measurement apparatus and a laser corneal surgery apparatus to give an example in the field of ophthalmology.

Having been described up to this point, according to the present invention, operability of apparatuses is improved even if a plurality of apparatuses are used for one patient. In addition, more space savings may be achieved as well as high usability.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A medical system for ophthalmic treatments, the system comprising:

a first ophthalmic treatment apparatus available for independent use in isolation from other apparatus, having a first treatment instrument for a first treatment and including a first setting unit which inputs a setting signal of a treatment condition, having a first display and a first memory which stores data on a setting screen for the treatment condition of the first treatment, a first footswitch which gives an operation signal, and first control means for controlling operation of the first treatment instrument based on the setting signal of the treatment condition from the first setting unit and the operation signal from the first footswitch;

a second ophthalmic treatment apparatus available for independent use in isolation from other apparatus, having a second treatment instrument for a second treatment and including a second setting unit which inputs a setting signal of a treatment condition, having a second display and a second memory which stores data on a setting screen for the treatment condition of the second treatment, a second footswitch which gives an operation signal, second control means for controlling operation of the second treatment instrument based on the setting signal of the treatment condition from the second setting unit and the operation signal from the second footswitch, and mode-selection means for selecting one of a mode for the second treatment and a mode for the first treatment; and a communication unit which connects the first treatment apparatus and the second treatment apparatus through cable communications or wireless communications, wherein the second treatment apparatus includes second detecting means for detecting the connection with the first treatment apparatus via the communication unit, in a case where the first treatment apparatus is actuated, the first control means calls up the setting screen for the first treatment condition from the first memory to the first display and controls the operation of the first treatment instrument based on the setting signal of the treatment condition from the first setting unit and the operation signal from the first footswitch, in a case where the second treatment apparatus is actuated, when the second treatment mode is selected by the mode-section means, regardless of a detection result of the second detecting means, the second control means calls up the setting screen for the second treatment condition from the second memory to the second display and controls the operation of the second treatment instrument based on the setting signal of the treatment condition from the second setting unit and the operation signal from the second footswitch, and when the first treatment mode is selected by the mode-selection means, if the connection with the first treatment apparatus and the actuation of the first treatment apparatus are detected by the second detecting means, the second control means calls up the setting screen for the first treatment condition from the first memory via the first control means to the second display and controls the operation of the first treatment instruction via the first control means based on the setting signal of the treatment condition from the second setting unit and the operation signal from the second footswitch, and one of the first and the second treatments is a treatment cutting and aspirating tissue inside an eye and the other one is a treatment irradiating a laser beam to a part inside the eye for photocoagulation.

2. The medical system according to claim 1, wherein the first and the second displays display respective setting screens for the first and the second treatment conditions in different colors.

3. The medical system according to claim 1, wherein the first treatment apparatus includes first detecting means for detecting the connection with the second treatment apparatus via the communication unit, and in a case where the first treatment apparatus is actuated, if the connection with the second treatment apparatus is not detected by the first detecting means, the first control means calls up the setting screen for the first treatment condition from the first memory to the first display and controls the operation of the first treatment instrument based on the setting signal of the treatment condition from the first setting unit and the operation signal from the first footswitch, and if the connection with the second treatment apparatus and the actuation of the second treatment apparatus or the selection of the second treatment mode are detected by the first detecting means, the first control means prevents the first display from displaying the setting screen for the first treatment condition and refuses the setting signal of the treatment condition from the first setting unit and the operation signal from the first footswitch.

* * * * *